(12) United States Patent
DeBernardis et al.

(10) Patent No.: US 6,228,878 B1
(45) Date of Patent: May 8, 2001

(54) METHODS FOR TREATING OR PREVENTING ALZHEIMER'S DISEASE USING SUBSTITUTED 2-ARYL-3-MORPHOLINOPROPANONES

(75) Inventors: John Francis DeBernardis, Lindenhurst; Daniel Joseph Kerkman, Lake Villa, both of IL (US)

(73) Assignee: Molecular Geriatrics Corporation, Vernon Hills, IL (US)

( * ) Notice: Subject to any disclaimer, the term of this patent is extended or adjusted under 35 U.S.C. 154(b) by 0 days.

(21) Appl. No.: 09/371,283

(22) Filed: Aug. 10, 1999

Related U.S. Application Data (63) Continuation of application No. 08/844,737, filed on Apr. 21, 1997, now Pat. No. 5,968,936, which is a continuation of application No. 08/341,493, filed on Nov. 17, 1994, now Pat. No. 5,705,501.

(51) Int. Cl.⁷ .................... A61K 31/405; A61K 31/435; A61K 31/40
(52) U.S. Cl. .................... 514/415; 514/277; 514/418; 514/414; 514/421
(58) Field of Search .................... 514/419, 415, 514/277, 421

(56) References Cited

U.S. PATENT DOCUMENTS

| | | | |
|---|---|---|---|
| 3,491,093 | 1/1970 | Pachter et al. | 260/247.5 |
| 5,462,934 | 10/1995 | Goto et al. | 514/183 |
| 5,681,954 | * 10/1997 | Yamamoto et al. | 514/114 |
| 5,705,501 | 1/1998 | DeBernardis et al. | 514/254.11 |
| 5,968,936 | 10/1999 | DeBernardis et al. | 514/232.2 |

FOREIGN PATENT DOCUMENTS

| | | |
|---|---|---|
| 0 560 235 | 9/1993 | (EP) . |
| 0 567 090 | 10/1993 | (EP) . |
| 0 607 864 | 7/1994 | (EP) . |

OTHER PUBLICATIONS

PTO Search Tool STN; Search of 4–oxoindole?, Jul. 2000.*

* cited by examiner

*Primary Examiner*—Theodore J. Criares
(74) *Attorney, Agent, or Firm*—McDonnell Boehnen Hulbert & Berghoff; Steven J. Sarussi (57) ABSTRACT

Disclosed are compounds of formula I:

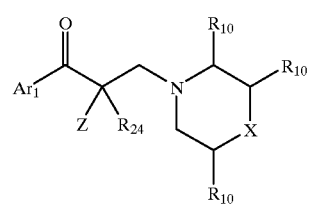

wherein
  X is selected from oxygen, sulfur and NR; wherein
    R is selected from hydrogen, loweralkyl and $CH_2CH_2COAr_1$; and
  Z is hydrogen; straight or branched chain alkyl having 1–6 carbon atoms; or Z and $R_1$, $R_2$ or $R_3$ together represent $CH_2$; $CH_2CH_2$; $CH_2O$; or $CH_2S$ forming a five or six membered ring and such ring may be optionally substituted with loweralkyl or phenyl;
  $R_{24}$ is hydrogen; loweralkyl, or optionally substituted phenyl;
  each $R_{10}$ is selected from hydrogen and loweralkyl; and
  $Ar_1$ represents an aryl group or optionally substituted phenyl, thienyl or optionally substituted thienyl; or the pharmaceutically acceptable salts thereof, useful for preventing or decreaseing the production of abnormally phosphorylated paired helical filament (PHF) epitopes associated with Alzheimer's Disease and, therefore, useful for treating Alzheimer's Disease.

2 Claims, 5 Drawing Sheets

PHF-1

METHODS FOR TREATING OR PREVENTING ALZHEIMER'S DISEASE USING SUBSTITUTED 2-ARYL-3-MORPHOLINOPROPANONES

This is a continuation of application Ser. No. 08/844,737 now U.S. Pat. No. 5,968,936 filed Apr. 21, 1997, which is a continuation of Ser. No. 08/341,493, filed Nov. 17, 1994, now U.S. Pat. No. 5,705,501.

BACKGROUND OF THE INVENTION

1. Field of the Invention

This invention relates to the use of certain 1-aryl-3-(4'-alkyl-1'-piperizinyl)-; 1-aryl-3-(4'-morpholinyl)-; and 1-aryl-3-(4'-thiomorpholinyl)-1-propanones in the treatment of Alzheimer's Disease.

2. Description of the Related Art

Alzheimer's Disease is a progressive neurodegenerative disorder affecting 7% of the population over 65 years of age and characterized clinically by progressive loss of intellectual function. This impairment of function is caused by the presence of neuritic plaques in the neocortex and the loss of presynaptic markers of cholinergic neurons. Neuritic plaques are composed of degenerating axons and nerve terminals, often surrounding an amyloid core and usually containing reactive glial elements. Another characteristic pathologic feature of Alzheimer's Disease is the neurofibrillary tangle, which is an intraneuronal mass which corresponds to an accumulation of abnormally phosphorylated tau protein polymerized into fibrillar structures termed paired helical filaments. In addition, the neurofibrillary tangle also contains highly phosphorylated neurofilament proteins. Even the earliest papers on Alzheimer's Disease were clear that both "senile" plaques and neurofibrillary tangles had to be present in abundance to allow a post-mortem diagnosis of the disease. Before any understanding of the molecular nature of these structures was obtained, efforts were being made to understand the relationship between the numbers of these lesions and the progression or severity of the dementia experienced by the patient. The limitations of silver staining were such that early workers in this field were unable to appreciate the complexity of these abnormal structures (Ball, M J, Neurobiol. of Aging, 8: 564–565, 1987). Although early attempts to correlate pathologic lesion counts with clinical symptoms generally yielded poor results, it was clear that the incidence of large numbers of both type lesions were invariably associated with dementia (Perry et al, J. Neural Transmission, 24: 131–136, 1987; Alafuzoff, I., Acta Neuropath, 74: 209–225, 1987; Whitehouse et al, Prog. Clin. Biol. Res., 317: 131–142. 1989; Tomlinson, Neuropathol. Appl. Neurobiol, 15: 491–512, 1989).

More recent work has allowed a clearer definition of the nature of the lesions stained by silver salts. "Senile" plaques are actually two distinct types of structures, the classical plaques described by Alzheimer being composed of degenerating neuronal elements (neurites) surrounding a central core of amyloid, while the other so-called "diffuse" or "primitive" plaque is usually a deposit of amyloid without a halo of degenerating neurites (Tagliavini, , et al, Neurosci. Lett., 93, 191–196, 1988; Dickson, D W, et al, Am. J. Path., 132, 86–101, 1988). These structures are difficult to distinguish from each other with silver stains or with the widely used fluorescent dye, thioflavin S. Early attempts, using silver staining, at correlations between plaque number and extent of dementia, as well as some more recent studies using thioflavin S, were flawed by this inability to define what type of plaque was being counted Hansen, L A, et al, Neurology, 38, 48–54, 1988; Katzman, R, et al, Ann. Neurol., 23, 138–144, 1988). This becomes very obvious in recent studies, which have consistently reported that amyloid plaques can be found in large numbers in the brains of the majority of the very elderly (over 80 years), and are only rarely associated with dementia when present without evidence of degenerating neurites (Davies, L, et al, Neurology, 38, 1688–1693, 1988; Delaere, P, et al, Neurosci. Lett., 116, 87–93, 1990; Dickson, D W, et al, Neurobiol. Aging, 13, 179–189, 1991).

The counting of neurofibrillary tangles also fails to give an accurate picture of the extent of neurofibrillary degeneration. Again, the presence of large numbers of tangles is invariably associated with a profound dementia, and some index of disease severity can be gained from tangle counts (Tomlinson, B E, Neuropathol. Appl. Neurobiol., 15, 491–512, 1989; Delaere, P, et al, Acta Neuropath., 77, 645–653, 1989). Electron microscopy first revealed that tangles were composed of masses of paired helical filaments (PHF) filling the cytoplasm of neurons (Terry, R D, et al, pages 145–155, In CIBA Foundation Symposium on Alzheimer's Disease and Related Conditions. Ed. by Wolstenholme, G E W, O'Conner, M, J and A Churchill, London, 1970). These studies also clearly showed that degenerating neurites also contained PHF, a fact only widely appreciated much later, when the use of antibodies to PHF became common (Wolozin, B L. et al, Science, 232, 648–650, 1986). Thus, both the plaques and the tangles of Alzheimer's Disease contain PHF. The use of antibodies to PHF also revealed the widespread presence of these paired helical filaments in neuronal processes (Brun, A, Prog. Clin. Biol. Res., 317, 285–293, 1989). Thus, the presence of PHF is much more widespread than was first suspected, and is today considered to be an indication of a widespread neuronal disease, of which the neuritic plaque and the neurofibrillary tangle are only the most obvious signs (McKee, A C, et al, Ann. Neurol., 30, 156–165, 1991). It has been estimated that as much as 90% of the PHF in the cortex of the average Alzheimer case is present in neuronal processes rather than in the plaque or tangle (Wolozin, B L, Ann. Neurol., 22, 521–526, 1987). Much of the early and indeed the present confusion with regard to diagnosis and severity of Alzheimer's Disease comes from the failure to appreciate the complexity of the pathology in this disease, although the occurrence of significant amounts of PHF in the brain is always associated with severe dementia (Hyman, B T, Current Opinions in Neurology and Neurosurgery, 5, 88–93, 1992). These results suggest that good correlations can be obtained between the concentration of PHF proteins (sometimes referred to as Alzheimer's Disease Associated Proteins or ADAP) in the cerebral cortex and the degree of dementia measured prior to the death of the patient (Ghanbari, H A, et al, JAMA, 263, 2907–2910, 1990).

It is noted that the terminology used to describe the abnormal protein complexes composing the fibrillar pathology in Alzheimer's Disease can be confusing. PHF is a morphological designation, describing abnormal filaments found in neurofibrillary tangles. An abnormal protein species migrating at 68 kDa, electrophoretically, and observed on immunoblots of tissue from AD brains was termed A68 (Wolozin, B, et al, Science, 232, 648–650, 1986). A protein complex shown to be specific for AD by immunochemical analyses was designated Alzheimer's Disease Associated Protein or by the acronym, ADAP (Ghanbari, H A, et al, JAMA, 263, 2907–2910, 1990). It is now known that A68 and ADAP, when viewed by the electron microscope, are PHFs. These PHFs have been further shown to contain, primarily, the microtubule-associated protein, tau. Hence, the terms A68. ADAP, PHF and PHF-tau are often used interchangeably. Thus, they are meant to be interchangable herein.

A series of important studies have suggested that the progression of Alzheimer's Disease can be defined pathologically by careful neuroanatomic studies of large numbers of brains from elderly humans, (Braak, H, et al, Neurosci. Lett., 103, 24–28, 1989; Braak, H, et al, Neuropath. and Applied Neurobiol., 15, 13–26, 1989; Braak, H, et al, Acta Neuropath., 82, 239–259, 1991; Braak, H, et al, European Neurology, 33, 403–408, 1993). The Braak's focus is almost entirely on the development of neurofibrillary pathology, which begins in the entorhinal cortex perhaps years before the clinical signs of the disease are apparent. The progression of Alzheimer's Disease is thought to be somewhat unusual, in the sense that the disease progresses by the involvement of more and more neurons in the formation of PHF, in an anatomic sequence which is to some extent predictable. In the initial stages, only those neurons of the entorhinal cortex contain PHF, in later stages, neurons of the CA1 and CA2 pyramidal layer of the hippocampus contain these structures, and still later, neurons of the association cortex begin to show evidence of PHF formation. Clearly, prevention of PHF formation even after the process is underway in the hippocampus could limit the disease to this brain region, at which point clinical problems are confined to some loss of short term memory. Patients first seek help at a stage when PHF pathology is largely limited to the hippocampus (Berg, L, et al, pages 9–25, in Alzheimer's Disease, Eds., Terry, R D; Katzman, R; Bick, K L. Raven Press, New York, 1994). To prevent the progression of Alzheimer's Disease at this point would clearly be a major benefit to the patient (Davies, P, pages 327–334, in Alzheimer's Disease, Eds., Terry, R D; Katzman, R; Bick, K L. Raven Press, New York, 1994; Khachaturian Z S, et al, pages 445–454, in Alzheimer's Disease, Eds., Terry, R D; Katzman, R; Bick, K L. Raven Press, New York, 1994).

Attempts to determine the molecular nature of the PHF were hampered at first by an approach which attempted to purify PHF from isolated neurofibrillary tangles. Once incorporated into the macromolecular complex that is the tangle, PHFs become extremely difficult to solubilize for protein analysis. The microtubule-associated protein tau appears to be a major antigenic component of PHF. The repeat region of microtubule-associated protein tau forms part of the core of the paired helical filament of Alzheimer's Disease (Goedert, M, et al, Proc. Nat'l. Acad. Sci., 85, 4051–4055, 1988; Wischik, C M, et al, Proc. Nat'l. Acad. Sci., 85, 4506–4510, 1988).

The involvement of protein phosphorylation in the formation of PHF has been suggested by a variety of studies which have shown that tau in PHF is hyperphosphorylated (Kosik, K S, et al, Ann. Med., 21, 109–112, 1989; Goedert, M, Trends in Neurosciences, 16, 460–465, 1993; Iqbal, K, et al, Act Neurobiologiae Experimentalis, 53, 325–335, 1993). There is suggestive evidence that several other proteins, especially neurofilaments and other microtubule associated proteins (MAPs) are also hyperphosphorylated in the brains of patients with Alzheimer's Disease (Lovestone, S, et al, Current Opinions in Neurology and Neurosurgery, 5, 883–888, 1992).

In 1985, a monoclonal antibody ALZ50 was raised (produced by hybridoma cell line ATCC No. HB9205) that recognized a 68 kDa polypeptide (termed A68) in immunoblots of the vulnerable brain regions in AD, but not in control brains, (Wolozin, B, et al, Science, 232, 648–650, 1986). Immunohistochemical analysis with this antibody indicated an intense reaction with neurofibrillary tangles and, in later experiments, with the PHF's, as well. The discovery of A68 was the first report of a biochemically determined abnormal protein species associated with the fibrillar pathology in AD.

In other laboratories in 1986, monoclonal and polyclonal antibodies recognizing the microtubule-associated protein, tau, were shown to react with neurofibrillary tangles, and subsequently, with PHFs (Grundke-Iqbal, I, et al, Proc. Nat'l,. Acad. Sci., 83, 4913–4917, 1986; Kosik, K S, et al, Proc. Nat'l. Acad. Sci., 83, 4044–4048, 1986). Furthermore, biochemical analyses of the protease-resistant "core" of the PHF demonstrated the presence of peptides containing the tau sequence, (Goedert, M, et al, Proc. Nat'l. Acad. Sci., 85, 4051–4055, 1988; Wischik, C M, et al, Proc. Nat'l. Acad. Sci., 85, 4506–4510, 1988). Additionally, monoclonal antibodies, whose epitopes spanned the tau molecule, all were shown to react with neurofibrillary tangles in AD brain (Kosik, K S, et al, Neuron, 1, 817–825, 1988). Much later, it was determined that the ALZ50 antibody reacts with the extreme amino terminus of the tau molecule, (Goedert, M, et al, Neuroscience Letters, 126, 149–154, 1991).

In 1990, in an attempt to purify A68, a more readily soluble preparation of PHFs was isolated (Greenberg, S and Davies, P, Proc. Nat'l. Acad. Sci., 87, 5827–5831, 1990). Immunoblots of these structures indicated that three closely migrating electrophoretic species, the slowest migrating of which was ca. 68 kDa in size, all reacted with ALZ50 and tau antibodies (Lee, V, et al, Science, 251, 675–678, 1991). This indicated that the A68 complex of proteins is, to a large extent, composed of the tau protein. This polymerized form of tau was shown over the years to be in a hyperphosphorylated state.

Other monoclonal antibodies raised against human PHF preparations are the antibodies PHF-1 and TG3. While these antibodies display robust affinity for paired helical filament preparations, they only have trace reactivity towards normal adult tau. Further studies revealed that the monoclonal antibody PHF-1 has a reduced affinity for PHF which has been treated with alkaline phosphatase or hydrofluoric acid, thereby suggesting that this antibody recognized a phosphorylated epitope(s) in paired helical filaments. These phosphorylated epitopes (recognized by PHF-1) reside within the C-terminal fragment of the tau protein, at serine 396 and 404 (Trojanowski, J. Q., et al, Clin. Neurosci., 1, 184–191, 1993). The epitope(s) recognized by TG3 has not been mapped yet.

To date, it has not been possible to consistently induce the formation of Alzheimer-like epitopes either in vivo or in vitro. Hence, there is a need for an assay for the determination of tau protein, paired helical filaments and mechanisms involved with Alzheimer's Disease. There is further a need for an assay suitable for screening for drugs which may prevent or decrease Alzheimer's Disease activity.

SUMMARY OF THE INVENTION

The compounds of this invention and an antipyschotic agent, chlorpromazine, are active in an assay indicative of the potential of certain drugs to inhibit a hallmark trait of Alzheimer's Disease. Further, chlorpromazine is shown herein to be capable of treating and/or preventing Alzheimer's Disease. Consequently, the compounds of this invention are useful for treating and/or preventing the disease.

The human neuroblastoma MSN1a cell line expresses the proteins known to be involved in PHF formation (including tau, other MAPs and neurofilament proteins, and thus is a cell line in which Alzheimer's Disease epitopes can be expressed. (Arias et al, J. Neurochem., 61: 673–682, 1993; Vincent et al, J. Neurochem., 62: 715–723, 1994).

Figure 1:
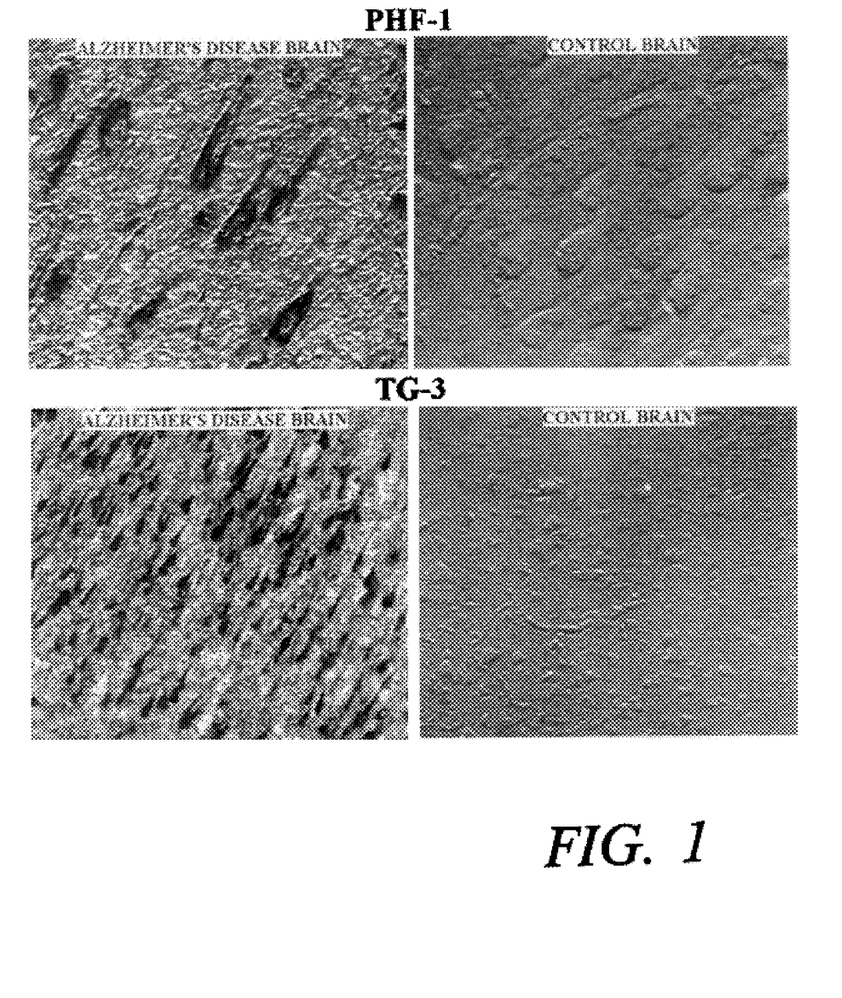
FIGS. 1A–1D are images produced by light microscopy showing immunohistochemical staining of brain tissue from normal Alzheimer's Disease patients with monoclonal antibodies PHF-1 and TG3.

Immunohistochemical staining of brains from normal and Alzheimer's Disease (AD) patients using the monoclonal antibodies PHF-1 and TG3 indicates that these monoclonal antibodies specifically stain elements of AD brain, but not normal brain (FIG. 1). Conditions were established which led to hyperphosphorylation of the proteins known to be involved in PHF formation. Using monoclonal antibodies PHF-1 and TG3 generated to human PHF preparations, the effects of a variety of manipulations of the phosphorylation state of these proteins were tested. These tests required that most of the abnormal epitopes recognized by these monoclonal antibodies in the human Alzheimer brain should be generated in the MSN1a cells. The treatment of MSN1a cells with okadaic acid and other selected inhibitors of protein phosphatases has been found to generate the epitopes associated with these Alzheimer brain specific monoclonal antibodies, thereby meeting the requirements described above. These epitopes are either absent or present at a very low level in untreated MSN1a cells.

Figure 2A:
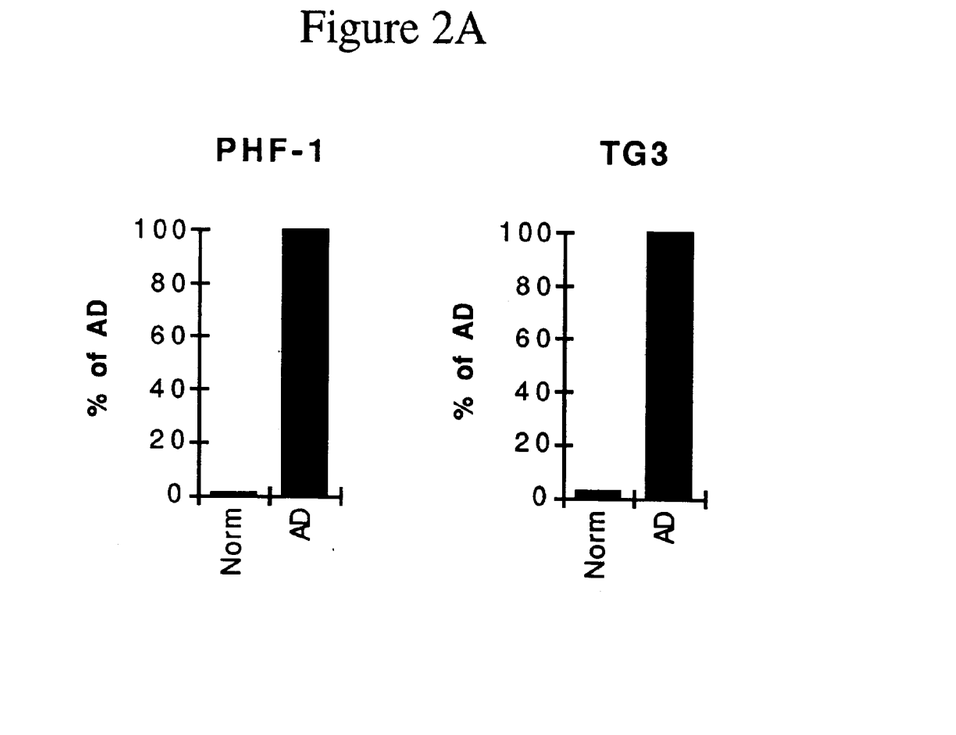
FIG. 2A is a graphic comparison of normal (Norm) and Alzheimer's Disease (AD) brain homogenate immunoreactivity toward PHF-1 and TG3 antibodies expressed as a percent of total AD immunoreactivity.
Figure 2B:
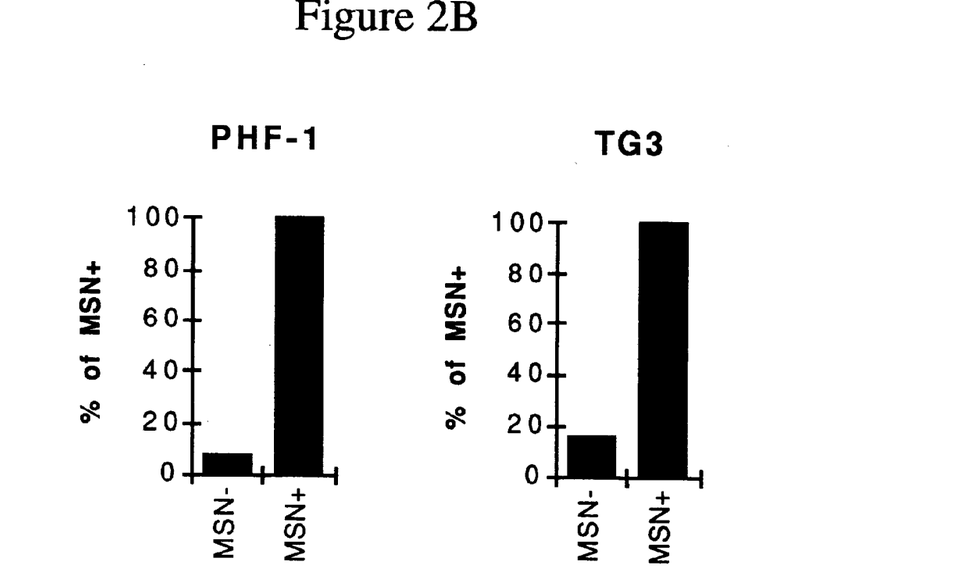
FIG. 2B is a graphic comparison of MSN1a cell lysate (minus or plus okadaic acid) immunoreactivity toward PHF-1 and TG3 antibodies expressed as a percent of total immunoreactivity in lysates of MSN+okadaic acid.

The AD specificity of the PHF-1 and TG3 antibodies was also demonstrated using an ELISA assay. Shown in FIG. 2A are bar graphs (percent of AD) of the ELISA immunoreactivity of brain preparations (AD or normal) to either PHF-1 or TG3. Shown in FIG. 2B are bar graphs (percent of MSN+) of the ELISA immunoreactivity of MSN1a cell preparations (minus or plus okadaic acid) to either PHF-1 or TG3. The MSN1a cell preparations plus vs minus okadaic acid closely parallel the AD vs normal brain preparations. This clearly shows the relationship between disease pathology (i.e. AD brain) and what is recognized by the antibodies in the MSN1a in vitro cell culture assay. The cell culture system according to the invention in which epitopes characteristic of PHF can be readily generated and subsequently recognized by the specific Alzheimer brain specific antibodies provides an assay suitable for screening compounds for their ability to block the production of these phosphorylated epitopes.

PHF tau protein has lower affinity for microtubules as compared to normal tau protein, which is likely the result of the abnormal phosphorylation (Lindwall et al, J. Biol. Chem., 259: 5301–5305, 1984). As a consequence, microtubule destabilization occurs which interferes with important neuronal processes such as rapid axonal transport and, subsequently, this process leads to the formation of PHF and the neurofibrillary tangles (Bancher, et al, Brain Res., 477, 90–99, 1989). Thus, inhibition of the production of the abnormal phosphorylated PHF epitopes will interfere with and/or prevent the formation of PHF. Since PHF formation is a major feature of Alzheimer pathology, the development of compounds that interfere with all or part of this process inhibit or prevent the progression of this disease.

The invention provides compounds of formula 1:

I or the pharmaceutically acceptable salts thereof wherein
  X is selected from oxygen, sulfur and NR, wherein
    R is selected from hydrogen, loweralkyl and $CH_2CH_2COAr_1$; and
  Z is hydrogen, straight or branched chain alkyl having 1–6 carbon atoms, or Z and a substituent on the aryl group together represent $CH_2$, $CH_2CH_2$, $CH_2O$, or $CH_2S$ to form a five or six membered ring where the ring is optionally substituted with loweralkyl or phenyl;
  $R_{24}$ is hydrogen, loweralkyl, or optionally substituted phenyl;
  each $R_{10}$ is selected from hydrogen and loweralkyl; and
  $Ar_1$ represents an aryl group or optionally substituted phenyl.

These compounds are useful for treating Alzheimer's Disease.

The compounds of this invention, by preventing or decreasing the production of abnormally phosphorylated paired helical filament epitopes associated with the production of the neurofibrillary tangles, a characteristic pathological feature of Alzheimer's Disease, are useful in the treatment of this neurodegenerative disorder.

The compounds of formula I inhibit and/or prevent the formation of abnormally phosphorylated epitopes on PHF tau. Through inhibitory interactions of the phosphorylation events associated with the formation of PHF tau, and other proteins involved in PHF formation, one can modulate the assembly of microtubules, thereby affecting neuronal processes such a rapid axonal transport, thus preventing the formation of PHF and the production of the neurofibrillary tangles. Thus, the compounds of the present invention are therapeutically useful in various neurodegenerative disorders such as Alzheimer's Disease.

Thus, the invention provides methods of preventing and/or treating Alzheimer's Disease in a patient comprising administering to the patient a compound of formula I in an amount effective to inhibit formation of abnormally phosphorylated paired helical filament epitopes.

DETAILED DESCRIPTION OF THE INVENTION

The invention provides compounds of formula I or the pharmaceutically acceptable salts thereof wherein X represents oxygen, sulfur and NR, wherein R is selected from hydrogen, loweralkyl and $CH_2CH_2COAr_1$;

Z is hydrogen; straight or branched chain alkyl having 1–6 carbon atoms; or Z and $R_1$, $R_2$ or $R_3$ together represent $CH_2$, $C(R_{24})_2CH_2$, $C(R_{24})_2O$, or $C(R_{24})_2S$ to form a five or six membered ring;

each $R_{10}$ independently represents hydrogen or loweralkyl; and

$Ar_1$ is a group of the formula:

wherein $R_1$, $R_2$ and $R_3$ independently represent hydrogen, halogen, nitro, cyano, alkoxy, phenoxy, benzoyloxy, benzyloxy, alkylsulfonylamino, trifluoromethyl, trifluoroalkoxy, thioloweralkoxy, thienyl, furyl, methylsulfinyl, phenyl, loweralkyl; or $Ar_1$ is a group of the formula:

wherein

Y is oxygen or sulfur

$Z_1$ is oxygen or methylene $R_4$ and $R_5$ are independently selected from hydrogen, halogen, loweralkoxy, hydroxy; and $R_6$, $R_7$, $R_8$, and $R_9$ are independently selected from hydrogen, halogen, nitro, cyano, loweralkyl, phenyl, optionally substituted phenyl, thienyl or optionally substituted thienyl, $R_{24}$ is hydrogen, loweralkyl, or optionally substituted phenyl.

The invention further encompasses compounds of formula II:

wherein:

$R_1$ is hydrogen, loweralkyl of 1 to 4 carbons, benzyl, phenyl or 2-, 3-, or 4-pyridyl;

$R_2$ and $R_3$ independently represent $C_1$–$C_8$ alkyl, $C_2$–$C_8$ alkenyl or $C_3$–$C_8$ cycloalkyl, phenyl, halogenatedphenyl or loweralkoxyphenyl;

$R_4$ is hydrogen or $C_1$–$C_4$ alkyl attached to carbon atom 6 or 7 of the indole nucleus;

X and Y are lower alkyl, hydroxy lower alkyl, lower acyloxy alkyl, carbamoyloxy lower alkyl and phenyl lower alkyl; or NXY represents a heterocyclic ring having a maximum of 8 members.

A preferred compound of formula II is 3-ethyl-4,5,6,7-tetrahydro-2-methyl-5-morpholinomethyl-4-oxoindole.

Methods for preparing the compound of formula II are described in U.S. Pat. No. 3,491,093.

The invention further encompasses compounds of formula III:

wherein $R_1$, $R_2$ and $R_3$ independently represent hydrogen, thioloweralkyl, nitro, halogen, trifluoromethyl, trifluoromethoxy, loweralkoxy, alkylsulfonylamido, methylsulfinyl, loweralkyl, phenyl, thienyl, or phenoxy.

The invention also encompasses compounds of formula IV:

wherein

R and $R_{10}$ are independently selected from hydrogen or loweralkyl; and $R_1$, $R_2$ and $R_3$ independently represent hydrogen, thioloweralkyl, nitro, halogen, trifluoromethoxy, trifluoromethyl, loweralkoxy, alkylsulfonylamido, methylsulfinyl, loweralkyl, phenyl, thienyl, or phenoxy.

The invention also encompasses compounds of formula V:

wherein $R_1$ is nitro or halogen.

The invention also encompasses compounds of formula VI wherein $R_1$ and $R_2$ are independently selected from hydrogen, loweralkyl or halogen.

The invention also encompasses compounds of formula VII wherein

R is $CH_2CH_2COAr_1$; and

$Ar_1$ is a group of the formula:

wherein $R_1$, $R_2$ and $R_3$ independently represent hydrogen, thioloweralkyl, nitro, halogen, trifluoromethyl, trifluoromethoxy, loweralkoxy, alkylsulfonylamido, methylsulfinyl, loweralkyl, phenyl, thienyl, or phenoxy.

The invention also encompasses compounds of formula VIII wherein

Z is oxygen, sulfur, methylene or a chemical bond; and $R_1$ is loweralkyl, hydrogen or halo.

The instant invention includes optically active compounds as well as racemic mixtures of such compounds. The invention further includes the pharmaceutically acceptable salts of such compounds or racemic mixtures. The invention still further includes pharmaceutical compositions comprising such compounds, salts thereof, or racemic mixtures thereof.

The numbering system used for the oxoindole rings of the invention is as follows:

As used herein, the term "loweralkyl" means straight or branched chain saturated hydrocarbon radicals having 1 to 4 carbon atoms, such as methyl, ethyl, n-propyl, t-butyl, and the like.

As used herein, the term "thioloweralkoxy" refers to $-SR_{11}$, wherein $R_{11}$ is loweralkyl.

As used herein, the term "halo or halogen" refers to fluorine, chlorine, bromine, or iodine.

As used herein, the term "alkylsulfonylamino" means $R_{12}S(O)_2NR_{13}-$ wherein $R_{12}$ is loweralkyl, phenyl, or substituted phenyl, and $R_{13}$ is hydrogen, loweralkyl or $-SO_2R_{12}$.

As used herein, the term "trifluoroalkoxy" refers to $-R_{14}CF_3$, wherein denotes a loweralkoxy group as defined above, attached to the parent molecular moiety through the oxygen atom. Representatives of such $R_{14}$ groups include, for example, methleneoxy, ethyleneoxy and the like.

As used herein, the term "Ar" or "aryl" refers to systems characterized by $4n+2\pi$ electrons, i.e., aromatic carbocyclic groups having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, hydroxy, lower alkyl, lower alkoxy, lower alkylthio, trifluoromethyl, lower acyloxy, aryl, and heteroaryl.

As used herein, the term "heteroaryl" means 5, 6, or 7 membered aromatic ring systems having at least one hetero atom selected from the group consisting of nitrogen, oxygen and sulfur. Examples of heteroaryl groups are pyridyl, pyrimidinyl, pyrrolo, pyrazolo, pyrazinyl, pyridazinyl, oxazolo, furanyl, quinoline, isoquinoline, thiazole, thiadiazole, isoxazole, and thienyl, which can optionally be unsubstituted or substituted with, e.g., halogen, hydroxy, lower alkyl, lower alkoxy, lower alkylthio, trifluoromethyl, lower acyloxy, cyano, nitro, aryl, and heteroaryl.

As used herein, the term "optionally substituted phenyl" refers to a phenyl ring having from zero to three substituents independently selected from loweralkyl, halogen, hydroxy, loweralkoxy, amino, thioloweralkoxy, nitro and cyano.

As used herein, the term "optionally substituted thienyl" refers to a thiophene ring with from zero to three substituents independently selected from loweralkyl, halo, phenyl, cyano and nitro.

As used herein, the term "optionally substituted phenoxy" refers to the phenoxy ring substituted as defined for optionally substituted phenyl.

The term "pharmaceutically acceptable salts" refers to the pharmaceutically acceptable, relatively non-toxic, inorganic, or organic acid addition salts of the compounds of this invention.

These salts can be prepared in situ during the final isolation and purification of the compounds or by separately reacting the free base with a suitable organic or inorganic acid. Representative salts include the hydrochloride, hydrobromide, sulfate, phosphate, nitrate, bisulfate, acetate, oxalate, valerate, oleate, palmitrate, methanesulfonate, stearate, laurate, borate, benzoate, lactate, phosphate, tosylate, citrate, maleate, fumarate, succinate, tartrate, napsylate, lactobionate, and the like. It will be apparent to those skilled in the art that, depending upon the number of available amino groups for salt formation, the salt of this invention can be per N-salts.

The present invention also provides pharmaceutical compositions which comprise one or more of the compounds of formula I above formulated together with one or more non-toxic pharmaceutically acceptable carriers. The pharmaceutical compositions may be specifically formulated for oral administration in solid or liquid form, for parenteral injection, or for rectal administration.

The pharmaceutical compositions of this invention can be administered to humans and other animals orally, rectally, parenterally (i.e. intravenously, intramuscularly, or subcutaneously), intracisternally, intravaginally, intraperitoneally, topically (as by powders, ointments, or drops), transdermally, bucally, or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Ophthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved. Generally dosage levels of about 0.1 to about 200, more preferably of about 0.5 to about 150, and most preferably about 1 to about 125 mg of active compound per kilogram of body weight per day are administered orally to a mammalian patient suffering from Alzheimer's Disease. If desired, the effective daily dose may be divided into multiple doses for purposes of administration, e.g. two to four separate doses per day.

All documents e.g., patents and journal articles, cited above or below are hereby incorporated by reference in their entirety.

One skilled in the art will recognize that modifications may be made in the present invention without deviating from the spirit or scope of the invention. The invention is illustrated further by the following examples which are not to be construed as limiting the invention or scope of the specific procedures described herein.

GENERAL PROCEDURE

As is more fully explained in the following scheme and examples, the compounds of the invention may be prepared by adding an appropriate secondary amine (1 mole) to a solution of concentrated hydrochloric acid (2–5 moles) in sufficient isopropanol to achieve an amine concentration of about 0.1 M–0.4 M. To the solution of amine hydrochloride salt which has been formed in situ is added paraformaldehyde (1–2.2 moles) followed by the desired aryl or heteroarylketone (1.1–2 moles), and the resulting reaction mixture is then refluxed for about 12–72 hours. The reaction is cooled and the resulting solid is filtered and recrystallized from methanol or triturated with methanol or ethanol to afford the desired product.

The compounds of the invention may be prepared according to the reactions set forth in the following reaction scheme.

where $Ar_1$, Z, X, and $R_{10}$ are as defined above for formula I.

Using the above-described procedure, the compounds described in the following examples were prepared.

EXAMPLE 1

1-Phenyl-3-(4'-methyl-1'-piperazinyl)-1-propanone dihydrochloride: A mixture of acetophenone (1.56 g, 12.98 mmol), 1-methylpiperazine (1.00 g, 9.98 mmol), paraformaldehyde (0.39 g, 12.98 mmol), and concentrated hydrochloric acid (4.16 mL, 0.05 mol) in 25 mL isopropanol were refluxed for 16 h. The reaction was cooled, filtered and the filter cake was basified (NH4OH), extracted with dicholormethane (2×75 mL), and purified via flash chromatography (silica; 8:2 EtOAC/MeOH). The free amine was converted to its dihydrochloride salt by the addition of dry ether/HCl to give 0.40 g (13%) of the desired product: mp 194–196° C.; $^1$H NMR of the free base (300 MHz, CDCl$_3$) δ 7.95 (d, 2 H), 7.6–7.35 (m, 3 H), 3.2 (t, 2 H), 2.85 (t, 2 H), 2.7–2.35 (brm, 8 H), 2.3 (s, 3 H).

EXAMPLE 2

1-(m-Methylphenyl)-3-(4'-methyl-1'-piperazinyl)-1-propanone dihydrochloride: mp 188° C. (dec.); $^1$H NMR of the free base (300 MHz, CDCl$_3$) δ 7.7 (m, 2 H), 7.35 (m, 2 H), 3.18 (t, 2 H), 2.85 (t, 2 H), 2.7–2.15 (brm, 14 H).

EXAMPLE 3

1-(p-Phenoxyphenyl)-3-(4'-methyl-1'-piperazinyl)-1-propanone dihydrochloride: mp 225° C. (dec.); $^1$H NMR of the free base (300 MHz, CDCl$_3$) δ 7.95 (d, 2 H), 7.40 (t, 2 H), 7.2 (t, 1 H), 7.15–6.95 (m, 4 H), 3.15 (t, 2 H), 2.85 (t, 2 H), 2.7–2.35 (brm, 8 H), 2.3 (s, 3 H).

EXAMPLE 4

1-Phenyl-3-(4'-n-propyl-1-piperazinyl)-1-propanone dihydrochloride: mp 200° C. (dec.); $^1$H NMR of the free base (300 MHz, CDCl$_3$) δ 7.95 (d, 2 H), 7.64–7.35 (m, 3 H), 3.2 (t, 2 H), 2.85 (t, 2 H), 2.7–2.15 (m, 10 H), 1.5 (septet, 2 H), 0.9 (t, 3 H).

EXAMPLE 5

1-(m-Methylphenyl)-3-(4'-propyl-1'-piperazinyl)-1-propanone dihydrochloride: mp 198° C. (dec.); $^1$H NMR of

EXAMPLE 6

1-(p-Phenoxyphenyl)-3-(4'-n-propyl-1'-piperazinyl)-1-propanone: mp 64–65° C.; $^1$H NMR (300 MHz, CDCl$_3$) δ 7.95 (d, 2 H), 7.4 (t, 2 H), 7.2 (t, 1 H), 7.15–6.90 (m, 4 H), 3.15 (t, 2 H), 2.85 (t, 2 H), 2.7–2.2 (m, 10 H), 1.5 (septet, 2 H), 0.90 (t, 3 H).

EXAMPLE 7

1-(3",4"-Dichlorophenyl)-3-(4'-methyl-1'-piperazinyl)-1-propanone hydrochloride: mp 205–207° C.; $^1$H NMR of the free base (300 MHz, CDCl$_3$) δ 8.05 (s, 1 H), 7.77 (d, 1 H), 7.55 (d, 1 H), 3.12 (t, 2 H), 2.82 (t, 2 H), 2.7–2.2 (m, 11 H).

EXAMPLE 8

1-(p-Chlorophenyl)-3-(4'-methyl-1'-piperazinyl)-1-propanone hydrochloride: mp 217–220° C.; $^1$H NMR (300 MHz, DMSO-d$_6$) δ 11.7 (brs, 2 H), 8.0 (d, 2 H), 7.7 (d, 2 H), 4.1–3.2 (brm, 12 H), 2.8 (s, 3 H).

EXAMPLE 9

1-(m-Methylphenyl)-3-(4'-morpholinyl)-1-propanone hydrochloride: A mixture of m-methylacetophenone (2.00 g, 0.015 mol), morpholine (1.00 g, 0.011 mol), paraformaldehyde (0.45 g, 0.015 mol), and concentrated hydrochloric acid (2.75 mL, 0.033 mol) in 25 mL isopropanol were refluxed for 3 h. The reaction was cooled, diluted with acetone (10 mL) and crystallized to give 1.90 g (64%) of the desired product: mp 176–179° C.; $^1$H NMR of the free base (300 MHz, CDCl$_3$) δ 7.77 (m, 2 H), 7.38 (m, 2 H), 3.7 (m, 4 H), 3.18 (t, 2 H), 2.82 (t, 2 H), 2.5 (m, 4 H), 2.4 (s, 3 H).

EXAMPLE 10

1-(m-Methylphenyl)-3-(1'-piperidyl)-1-propanone hydrochloride: mp 154–158° C.; 1H NMR of the free base (300 MHz, CDCl$_3$) δ 7.77 (m, 2 H), 7.36 (m, 2 H), 3.2 (t, 2 H), 2.8 (t, 2 H), 2.6–2.3 (m, 7 H), 1.7–1.35 (m, 6 H).

EXAMPLE 11

1-(p-Phenoxyphenyl)-3-(4'-morpholinyl)-1-propanone hydrochloride: mp 165–170° C.; $^1$H NMR of the free base (300 MHz, CDCl$_3$) δ 7.95 (d, 2 H), 7.4 (t, 2 H), 7.2 (t, 1 H), 7.15–6.95 (m, 4 H), 3.72 (m, 4 H), 3.15 (t, 2 H), 2.83 (t, 2 H), 2.5 (m, 4 H).

EXAMPLE 12

1-(p-Fluorophenyl)-3-(4'-morpholinyl)-1-propanone hydrochloride: mp 202° C. (dec.); $^1$H NMR (300 MHz, DMSO-d$_6$) δ 10.1 (brs, 1 H), 8.1 (m, 2 H), 7.4 (m, 2 H), 4.0 (m, 2 H), 3.8–3.3 (m, 10 H).

EXAMPLE 13

1-(o-Methoxyphenyl)-3-(4'-morpholinyl)-1-propanone hydrochloride: mp 161–163° C.; $^1$H NMR of the free base (300 MHz, CDCl$_3$) δ 7.68 (dd, 1 H), 7.45 (m, 1 H), 6.99 (m, 2 H), 3.9 (s, 3 H), 3.7 (m, 4 H), 3.2 (t, 2 H), 2.78 (t, 2 H), 2.48 (m, 4 H).

EXAMPLE 14

1-(m-Methoxyphenyl)-3-(4'-morpholinyl)-1-propanone hydrochloride: mp 165–167° C.; $^1$H NMR of the free base (300 MHz, CDCl$_3$) δ 7.52 (m, 2 H), 7.4 (t, 1 H), 7.12 (m, 1 H), 3.87 (s, 3 H), 3.7 (m, 4 H), 3.2 (t, 2 H), 2.83 (t, 2 H), 2.5 (m, 4 H).

EXAMPLE 15

1-(p-Methanesulfonamidophenyl)-3-(4'-morpholinyl)-1-propanone hydrochloride: mp 215–218° C.; $^1$H NMR (300 MHz, DMSO-d$_6$) δ 11.1 (brs 1 H), 10.45 (s, 1 H), 8.0 (d, 2 H), 7.35 (d, 2 H), 4.1–3.2 (brm 12 H), 3.1 (s, 3 H).

EXAMPLE 16

1-(3",4"-Dichlorophenyl)-3-(4'-morpholinyl)-1-propanone hydrochloride: mp 190–191° C.; $^1$H NMR (300 MHz, DMSO-d$_6$) δ 10.6 (brs 1, H), 8.25 (dd, I H), 7.9 (m, 2 H), 4.0 (m, 2 H), 3.85–3.0 (brm, 10 H).

EXAMPLE 17

1-(2",5"-Dichlorophenyl)-3-(4'-morpholinyl)-1-propanone hydrochloride: mp 163° C. (dec.); $^1$H NMR of the free base (300 MHz, CDCl$_3$) δ 5–7.3 (m, 3 H), 3.68 (m, 4 H), 3.12 (t, 2 H), 2.75 (t, 2 H), 2.44 (m, 4 H).

EXAMPLE 18

1-(p-Chlorophenyl)-3-(4'-morpholinyl)-1-propanone: mp 90–91° C.; $^1$H NMR (300 MHz, CDCl$_3$) δ 7.9 (d, 2 H), 7.45 (d, 2 H), 3.71 (m, 4 H), 3.16 (t, 2 H), 2.84 (t, 2 H), 2.5 (m, 4 H).

EXAMPLE 19

1-(3"-Thienyl)-3-(4'-morpholinyl)-1-propanone hydrochloride: mp 192–194° C.; $^1$H NMR (300 MHz, D$_2$O) δ 8.3 (s, 1 H), 7.43 (m, 2 H), 3.85 (brs, 4 H), 3.55–3.1 (brm, 8 H).

EXAMPLE 20

1-p-Nitrophenyl)-3-(4'-thiomorpholinyl)-1-propanone hydrochloride: mp 203–205° C.; $^1$H NMR (300 MHz, D$_2$O) δ 8.23 (d, 2 H), 8.05 (d, 2 H), 3.18–3.15 (brm, 8 H), 3.1–2.6 (brs, 4 H).

EXAMPLE 21

1-(m-Nitrophenyl)-3-(4'-methyl-1'-piperazinyl)-1-propanone dihydrochloride: mp 210–212° C.; 1H NMR (300

MHz, DMSO-4) δ 12.00–11.40 (brs, 2 H), 8.70 (s, I H), 8.55 (d, 1 H), 8.40 (d, 1 H), 7.90 (dd, 1 H), 4.00–3.20 (m, 12 H), 2.85 (s, 3 H).

EXAMPLE 22

1-(p-Methylphenyl)-3-(4'-methyl-1'-piperazinyl)-l-propanone dihydrochloride: mp 199–200° C.; $^1$H NMR (300 MHz, DMSO-$d_6$), δ 12.15–7.5 (brs, 2 H), 7.90 (d, 2 H), 7.35 (d, 2 H), 4.05–3.15 (m, 12 H), 2.85 (s, 3 H), 2.35 (s, 3 H).

EXAMPLE 23

1-(o-Fluorophenyl)-3-(4'-methyl-1'-piperazinyl)-1-propanone dihydrochloride: mp 198–200° C.; $^1$H NMR (300 MHz, DMSO-$d_6$) δ 11.90–11.50 (brs, 2 H), 8.00–6.5 (m, 2 H), 7.50–7.30 (m, 2 H), 3.90–3.15 (m, 12 H), 2.80 (s, 3 H).

EXAMPLE 24

1-(m-Nitrophenyl)-3-(4'-n-propyl-1'-piperazinyl)-l-propanone dihydrochloride: mp 200–203° C.; $^1$H NMR (300 MHz, DMSO-$d_6$) δ 12.20–11.50 (brs, 2 H), 8.75 (s, 1 H), 8.55 (d, 1 H), 8.40 (d, 1 H), 7.90 (dd, 1 H), 4.00–2.90 (m, 14 H), 1.72 (m, 2 H), 0.93 ((s 3 H).

EXAMPLE 25

1-(m-Benzoyloxyphenyl) -3-(4'-n propyl-1'-piperazinyl)-1-propanone dihydrochloride: mp 215–218° C.; $^1$H NMR (300 MHz, DMSO-$d_6$) δ 12.00–11.30 (brs, 2 H), 8.12 (d, 2 H), 8.00–7.50 (m, 7 H), 4.00–2.90 (m, 14 H), 1.85–1.75 (m, 2 H), 0.91 (t, 3 H).

EXAMPLE 26

1-(m-Nitrophenyl)-3-(2',6'-dimethyl-4'-piperazinyl)-1-propanone dihydrochloride: mp 210° C. (dec.); $^1$H NMR (300 MHz, DMSO-$d_6$) δ 12.30–12.00 (brs, 1 H), 10.20–10.00 (brs, 1 H), 10.00–9.70 (brs, 1 H), 8.70 (s, 1 H), 8.54 (d, 1 H), 8.43 (d, 1 H), 7.90 (dd, 1 H), 4.10–2.90 (m, 10 H), 1.30 (d, 6 H).

EXAMPLE 27

1-(o-Fluorophenyl)-3-(2',6'-dimethyl-4'-piperazinyl)-1-propanone dihydrochloride: mp 215° C. (dec.); $^1$H NMR (300 MHz, DMSO-$d_6$) δ 12.15 (brs, 1 H), 10.05–9.75 (brs, 1 H), 10.25–10.05 (brs, 1 H), 7.95–7.65 (m, 2 H), 7.50–7.30 (m, 2 H), 3.90–2.95 (m, 10 H), 1.30 (d, 6 H).

EXAMPLE 28

1-(m-Chlorophenyl)-3-(4'-methyl-1'-piperazinyl)-1-propanone dihydrochloride: mp 200–205° C.; $^1$H NMR (300 MHz, DMSO-$d_6$) δ 12.30–11.60 (brs, 2 H), 8.04 (s, 1 H), 7.95 (d, 1 H), 7.75 (d, 1 H), 7.60 (dd, 1 H), 4.00–3.10 (m, 12), 2.80 (s, 3 H).

EXAMPLE 29

1-(p-Bromophenyl)-3-(4'-methyl-1'-piperazinyl)-1-propanone dihydrochloride: mp 216–220° C.; $^1$H NMR (300 MHz, DMSO-$d_6$) δ 12.35–11.73 (brs, 2 H), 7.90 (d, 2 H), 7.79 (d, 2 H), 6.00–3.05 (m, 12 H), 2.80 (s, 3 H).

EXAMPLE 30

1-(m-Nitrophenyl)-3-(4'-morpholinyl)-1-propanone hydrochloride: mp 194–195° C.; $^1$H NMR (300 MHz, DMSO-$d_6$) δ 11.25–11.50 (brs, 1 H), 8.75 (s, 1 H), 8.55 (d, 1 H), 8.42 (d, 1 H), 7.90 (dd, 1 H), 4.10–3.40 (m, 10 H), 3.25–3.00 (m, 2 H).

EXAMPLE 31

1-(p-Methylphenyl)-3-(4'-morpholinyl)-1-propanone hydrochloride: mp 202–204° C.; $^1$H NMR (300 MHz, DMSO-$d_6$) δ 11.60–11.30 (brs, 1 H), 7.82 (d, 2 H), 7.35 (d, 2 H), 4.11–3.00 (m, 12 H), 2.40 (s, 3 H).

EXAMPLE 32

1-(o-Fluorophenyl)-3-(4'-morpholinyl)-1-propanone hydrochloride: mp 185–187° C.; $^1$H NMR (300 MHz, DMSO-$d_6$) δ 11.55–11.30 (brs, 1 H), 7.88–7.55 (m, 2 H), 7.50–7.22 (m, 2 H), 4.10–3.32 (m, 10 H), 3.25–3.00 (m, 2 H).

EXAMPLE 33

1-(m-Methanesulfonamidophenyl)-3-(4'-morpholinyl)-1-propanone hydrochloride: mp 209–210° C.; $^1$H NMR (300 MHz, DMSO-$d_6$) δ 11.35–11.17 (brs, 1 H), 10.15 (s, 1 H), 7.90–7.70 (m, 2 H), 7.60–7.40 (m, 2 H), 4.10–3.20 (m, 10 H), 3.20–3.00 (m, 2 H), 3.00 (s, 3 H).

EXAMPLE 34

1-[m-(N-Methyl-N-methylsulfonylamino)phenyl]-3-(4'-morpholinyl)-1-propanone hydrochloride: mp 174–175° C.; $^1$H NMR (300 MHz, DMSO-$d_6$) δ 11.25–11.05 (brs, 1 H), 8.10–7.90 (m, 2 H), 7.75 (d, 1 H), 7.65 (dd, 1 H), 4.10–3.40 (m, 10 H), 3.30 (s, 3 H), 3.23–3.05 (m, 2 H), 3.00 (s, 3 H).

EXAMPLE 35

1-(p-Methylthiophenyl)-3-(4'-morpholinyl)-1-propanone hydrochloride: A mixture of p-methylthioacetophenone (1.10 g, 7.46 mmol), morpholine (0.50 g, 5.74 mmol, 0.05 ml), paraformaldehyde (0.34 g, 11.33 mmol) and concentrated hydrochloric acid (1.43 ml) in 30 ml. isopropanol were refluxed for 48 h. The reaction was cooled, filtered and the filter cake was triturated with acetone to give 1.10 g (~64%) of the desired product: mp 200–202° C.; $^1$H NMR (300 MHz, DMSO-$d_6$) δ 11.40–11.05 (brs 1 H), 7.93 (d, 2 H), 7.40 (d, 2 H), 4.10–3.32 (m, 10 H), 3.20–3.00 (m, 2 H), 2.55 (s, 3 H).

EXAMPLE 36

1-(p-Methoxyphenyl)-3-(4'-morpholinyl)-1-propanone hydrochloride: mp 207–210° C.; 1H NMR (300 MHz, DMSO-$d_6$) δ 11.30–11.10 (brs, 1 H), 8.00 (d, 2 H), 7.10 (d, 2 H), 4.10–3.05 (m, 12 H), 3.85 (s, 3 H).

EXAMPLE 37

1-(4"-Fluoronaphth-1"-yl)-3-(4'-morpholinyl)-1-propanone hydrochloride: mp 180–182° C.; $^1$H NMR (300

MHz, DMSO-$d_6$) δ 11.00–10.95 (brs, 1 H), 8.75 (d, 1 H), 8.40–8.25 (m, 1 H), 8.15 (d, 1 H), 7.70 (m, 2 H), 7.60–7.50 (m, 1 H), 4.00–3.10 (m, 12 H).

EXAMPLE 38

1-(m-Chlorophenyl)-3-(4'-morpholinyl)-1-propanone hydrochloride: mp 188–190° C.; $^1$H NMR (300 MHz, DMSO-$d_6$) δ 11.25–11.00 (brs, 1 H), 8.05 (s, 1 H), 7.95 (d, 1 H), 7.75 (d, 1 H), 7.65 (dd, 1 H), 4.10–3.05 (m, 12 H).

EXAMPLE 39

1-(1'',2'',3'',4''-Tetrahydronaphth-6''-yl)-3-(4'-morpholinyl)-1-propanone hydrochloride: mp 190° C.; $^1$H NMR (300 MHz, CDCl$_3$) δ 13.40–13.10 (brs, 1 H), 7.80–7.60 (m, 2 H), 7.16 (d, 1 H), 4.30 (t, 2 H), 4.10–3.90 (m, 2 H), 3.76 (t, 2 H), 3.60–3.30 (m, 4 H), 3.10–2.70 (m, 6 H), 1.90–1.70 (brs, 4 H).

EXAMPLE 40

1-(p-Trifluoromethoxyphenyl)-3-(4'-morpholinyl)-1-propanone hydrochloride: mp 175–178° C.; $^1$H NMR (300 MHz, DMSO-$d_6$) δ 11.15–10.90 (brs 1 H), 8.15 (d, 2 H), 7.55 (d, 2 H), 4.08–3.40 (m, 10 H), 3.25–3.00 (m, 2 H).

EXAMPLE 41

1-(2'',3''-Dihydro-1'',4''-benzodioxan-6''-yl)-3-(4'-morpholinyl)-1-propanone hydrochloride: mp 223–225° C.; $^1$H NMR (300 MHz, DMSO-$d_6$) δ 11.25–11.50 (brs, 1 H), 7.65–7.40 (m, 2 H), 7.05 (d, 1 H), 4.50–4.15 (m, 4 H), 4.05–3.30 (m, 10 H), 3.20–3.00 (m, 2 H).

EXAMPLE 42

1-(p-Bromophenyl)-3-(4'-morpholinyl)-1-propanone hydrochloride: mp 209–212° C.; $^1$H NMR (300 MHz, DMSO-$d_6$) δ 11.55–11.30 (brs, 1 H), 7.95 (d, 2 H), 7.75 (d, 2 H), 4.10–3.35 (m, 10 H), 3.25–3.00 (m, 2 H).

EXAMPLE 43

1-(p-Ethylphenyl)-3-(4'-morpholinyl)-1-propanone hydrochloride: mp 202–205° C.; $^1$H NMR (300 MHz, DMSO-$d_6$) δ 11.65–11.35 (brs, 1 H), 7.95 (d, 2 H), 7.40 (d, 2 H), 4.08–3.30 (m, 10 H), 3.25–3.00 (m, 2 H), 2.70 (q, 2 H), 1.20 (t, 3 H).

EXAMPLE 44

1,4-Bis-(3'-Phenylpropane-3'-one-1'-yl)-piperazine dihydrochloride: A mixture of acetophenone (3.49 g, 0.029 mol), piperazine (1.00 g, 0.012 mol), paraformaldehyde (0.87 g, 0.029 mol), and concentrated hydrochloric acid (5.00 mL, 0.06 mol) were refluxed for 24 h. The reaction was cooled, filtered and the filter cake was triturated with methanol to give 3.5 g (83%) of the desired product: mp 230° C. (dec.); $^1$H NMR of the free base (300 MHz, CDCl$_3$) δ 7.96 (d, 4 H), 7.51 (m, 6 H), 3.19 (t, 4 H), 2.85 (t, 4 H), 2.58 (brs, 8 H).

EXAMPLE 45

1,4-Bis-(3'-Phenylpropane-3'-one-1'-yl)-2,5-dimethylpiperazine dihydrochloride: mp 250° C.; $^1$H NMR of the free base (300 MHz, CDCl$_3$) δ 7.98 (d, 4 H), 7.51 (m, 6 H), 3.21 (m, 6 H), 2.82 (m, 4 H), 2.49 (m, 2 H), 2.14 (t, 2 H), 1.08 (d, 6 H).

EXAMPLE 46

1,4-Bis-(3'-p-fluorophenylpropane-3'-one-1'-yl)-piperazine: mp 170–173° C.; $^1$H NMR (300 MHz, CDCl$_3$) δ 7.98 (m, 4 H), 7.13 (m, 4 H), 3.18 (t,4 H), 2.86(t, 4 H), 2.59 (brs, 8 H).

EXAMPLE 47

1,4-Bis-[3'-(3'',4''-dichlorophenyl)-propane-3'-one-1'-yl]-piperazine dihydrochloride: mp>230° C.; $^1$H NMR of the free base (300 MHz, CDCl$_3$) δ 8.03 (d, 2 H), 7.78 (dd, 2 H), 7.55 (d, 4 H), 3.14 (t, 4 H), 2.82 (t, 4 H), 2.56 (brs, 8 H).

EXAMPLE 48

1,4-Bis-(3'-p-chlorophenylpropane-3'-one-1'-yl)-piperazine dihydrochloride: mp>230° C.; $^1$H NMR of the free base (300 MHz, CDCl$_3$) δ 7.9 (d, 4 H), 7.43 (d, 4 H), 3.15 (t, 4 H), 2.84 (t, 4 H), 2.56 (brs, 8 H).

EXAMPLE 49

1,4-Bis-(3'-m-chlorophenylpropane-3'-one-1'-yl) piperazine: mp 121–122° C.; $^1$H NMR (300 MHz, CDCl$_3$) δ 7.95 (s, 2 H), 7.82 (d, 2 H), 7.55 (d, 2 H), 7.40 (t, 2 H), 3.15 (t, 4 H), 2.85 (t, 4 H), 2.70–2.40 (brs, 8 H).

EXAMPLE 50

1,4-Bis-(3'-p-bromophenylpropane-3'-one-1'-yl) piperazine: mp 158–160° C.; $^1$H NMR (300 MHz, CDCl$_3$) δ 7.85 (d, 4 H), 7.60 (d, 4 H), 3.15 (t, 4 H), 2.85 (t, 4 H), 2.65–2.40 (brs, 8 H).

EXAMPLE 51

1,4-Bis-(3'-p-methylphenylpropane-3'-one-1'-yl) piperazine: mp 229–231° C.; 1H NMR (300 MHz, CDCl$_3$) δ 7.86 (d, 4 H), 7.26 (d, 4 H), 3.17 (t, 4 H), 2.83 (t, 4 H), 2.67–2.45 (brs, 8 H), 2.40 (s, 6 H).

EXAMPLE 52

1,4-Bis-(3'-o-fluorophenylpropane-3'-one-1'-yl) piperazine: $^1$H NMR (300 MHz, DMSO-$d_6$) δ 7.85–7.55 (m, 4 H), 7.40–7.20 (m, 4 H), 3.10 (t, 4 H), 2.62 (t, 4 H), 2.43–2.20 (brs, 8 H).

EXAMPLE 53

1,4-Bis-(3'-m-nitrophenylpropane-3'-one-1'-yl) piperazine: mp 154–155° C.; $^1$H NMR (300 MHz, CDCl$_3$) δ 8.80 (s, 2 H), 8.42 (d, 2 H), 8.27 (d, 2 H), 7.69 (t, 2 H), 3.21 (t, 4 H), 2.56 (t, 4 H), 2.70–2.40 (brs 8 H).

EXAMPLE 54

1-p-Nitrophenyl)-3-(4'-methyl-1'-piperazinyl)-1-propanone dihydrochloride: mp 225–226° C.; $^1$H NMR (300 MHz, DMSO-d$_6$) δ 12.1 (s, 2 H), 8.4 (d, 2 H), 8.2 (d, 2 H), 4.25–3.18 (m, 12 H), 2.85 (s, 3H).

EXAMPLE 55

1-(p-Nitrophenyl)-3-(2',6'-dimethyl-4'-piperazinyl)-1-propanone dihydrochloride: mp>260° C.; $^1$H NMR (300 MHz, D$_2$O) δ 7.95 (d, 2 H), 7.78 (d, 2 H), 3.58 (m, 2 H), 3.39 (m, 6 H), 2.83 (t, 2 H).

EXAMPLE 56

1-(p-Nitrophenyl)-3-(4'-morpholinyl)-1-propanone hydrochloride: mp 214–216° C.; $^1$H NMR (300 MHz, D$_2$O) δ 8.2 (d, 2 H), 8.02 (d, 2 H), 4.1–3.0 (m, 12 H).

EXAMPLE 57

1-(p-Iodophenyl)-3-(4'-methyl-1'-piperazinyl)-1-propanonedihydrochloride: mp224–225° C.; $^1$H NMR (300 MHz, DMSO-d$_6$) δ 11.94 (brs, 2 H), 7.99 (d, 2 H), 7.87 (d,. 2 H), 4.18–3.05 (brm, 12 H), 2.81 (s, 3 H).

EXAMPLE 58

1-(p-Iodophenyl)-3-(4'-morpholinyl)-1-propanone hydrochloride: mp 224–225° C.; $^1$H NMR (300 MHz, DMSO-d$_6$) δ 11.09 (s, 1 H), 8.02 (d, 2 H), 7.89 (d, 2 H), 4.10–2.95 (m, 12 H).

EXAMPLE 59

1-(m-Fluorophenyl)-3-(4'-methyl-1'-piperazinyl)-1-propanonedihydrochloride: mp 189–190° C.; $^1$H NMR (300 MHz, DMSO-d$_6$) δ 11.95 (s, 2 H), 4.0–3.1 (m, 12 H), 2.8 (s, 3 H).

EXAMPLE 60

1-(m-Fluorophenyl)-3-(4'-morpholinyl)-1-propanone hydrochloride: mp 185–186° C.; $^1$H NMR of the free base (300 MHz, CDCl$_3$) δ 7.75 (m, 1 H), 7.64 (m, 1 H), 7.46 (m, 1 H), 7.28 (m, 1 H), 3.7 (m, 4 H), 3.18 (t, 2 H), 2.83 (t, 2 H), 2.51 (m, 4 H).

EXAMPLE 61

1-p-Biphenyl-3-(4'-morpholinyl)-1-propanone hydrochloride: mp 192–194° C.; $^1$H NMR of the free base (300 MHz, CDCl$_3$) δ 8.05 (d, 2 H), 7.67 (dd, 4 H), 7.45 (m, 3 H), 7.73 (m, 4 H), 3.22 (t, 2 H), 2.86 (t, 2 H), 2.53 (m, 4 H).

EXAMPLE 62

21-p-Biphenyl-3-(4'-methyl-1'-piperazinyl)-1-propanone: The solid was basified with NH$_4$OH, extracted with dichloromethane and evaporated and dried: mp 103–104° C.; $^1$H NMR (300 MHz, CDCl$_3$) δ 8.03 (d, 2 H), 7.67 (dd, 4 H), 7.44 (m, 2 H), 3.23 (t, 2 H), 2.9 (t, 2 H), 2.54 (m, 8 H), 2.31 (s, 3 H).

EXAMPLE 63

1-(p-Methylsulfonamidophenyl)-3-(4'-methyl-1'-piperazinyl)-1-propanone dihydrochloride: mp 199–200° C., $^1$H NMR (300 MHz, CDCl$_3$) δ 11.9 (s, 2 H), 10.28 (s, 1 H), 8.0 (d, 2 H), 7.25 (d, 2 H), 4.8–2.6 (m, 18 H).

EXAMPLE 64

1-(m-Fluorophenyl)-3-(2',6'-dimethyl-4'-piperazinyl)-1-propanone dihydrochloride: mp>235° C. (dec.); $^1$H NMR (300 MHz, DMSO-d$_6$) δ 9.88 (m, 2 H), 7.8 (dd. 2 H), 7.6 (m, 2 H), 4.08–2.9 (m, 10 H), 1.31 (d, 6 H).

EXAMPLE 65

1,4-Bis-(3'-m-fluorophenylpropane-3'-one-1'-yl) piperazine: The solid was basified with NH$_4$OH, extracted with dichloromethane, dried and filtered: mp 111–1 12° C.; $^1$H NMR (300 MHz, CDCl$_3$) δ 7.72 (d, 2 H), 7.63 (m, 2 H), 7.45 (m, 2 H), 7.28 (m, 2 H), 3.18 (t, 4 H), 2.86 (t, 2 H), 2.57 (brm, 8 H).

EXAMPLE 66

1,4-Bis-(3'-p-Nitrophenylpropane-3'-one-1'-yl) piperazine: The solid was basified with NOH, extracted with dichloromethane and purified via flash chromatography (Silica, 9:1 EtOAc:MeOH): mp 185–186° C. (dec.); $^1$H NMR (300 MHz, CDCl$_3$) δ 8.32 (d, 4 H), 8.11 (d, 4 H), 3.23 (t, 4 H), 2.86 (t, 4 H), 2.57 (brs, 8 H).

EXAMPLE 67

Effect of Chlorpromazine on Paired Helical Filament Levels in Human Brain Tissue The in vitro analyses described herein to investigate the activity of the compounds of this invention can also be used to determine the nature of abnormally phosphorylated paired helical filament epitopes involved in Alzheimer's Disease, the regulatory mechanisms involved with Alzheimer's Disease and modifications of the protein tau and other polypeptides associated with PHFs and involved in Alzheimer's Disease.

Figure 3:
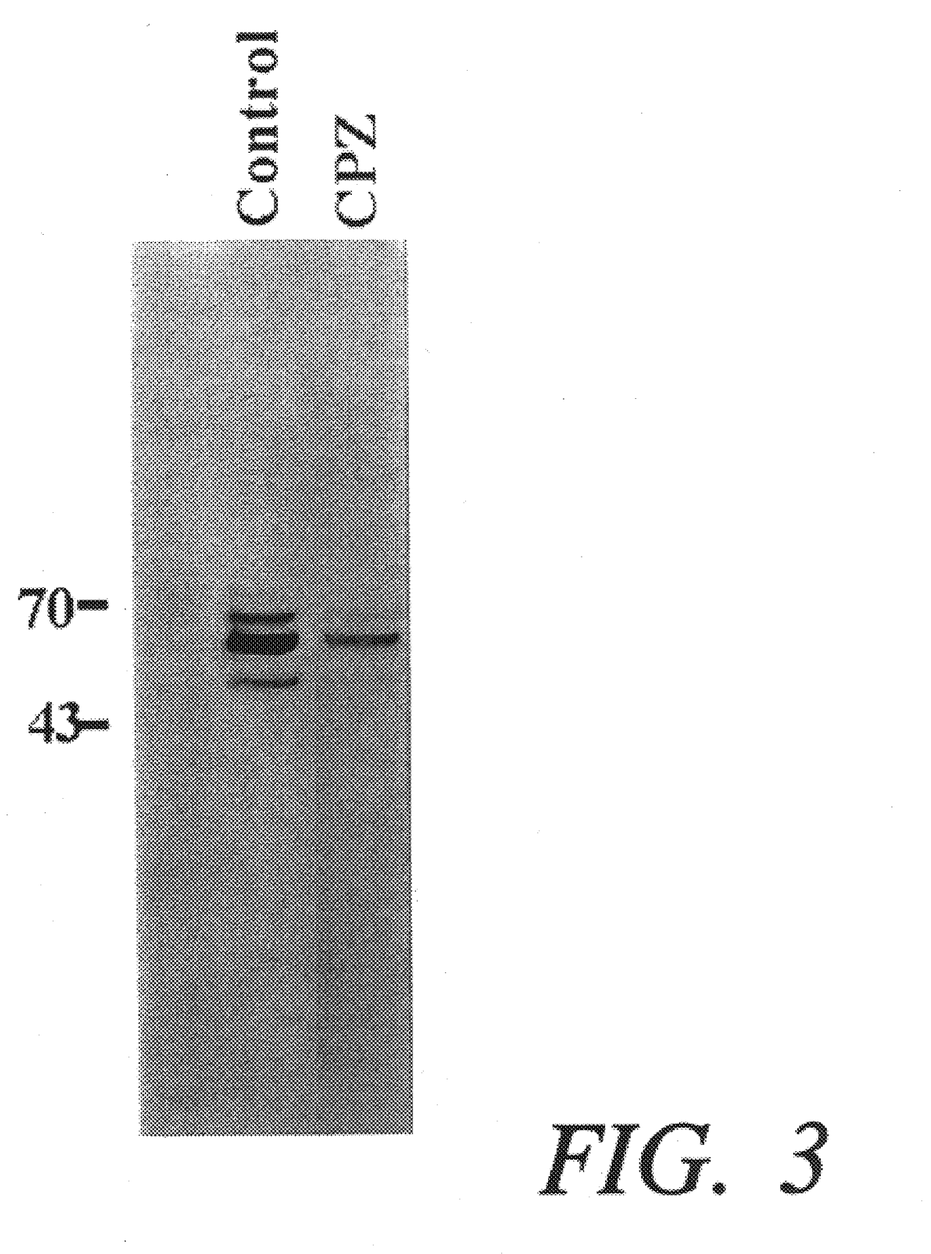
FIG. 3 is a western blot showing PHF-1 immunoreactivity in lysates from control and chlorpromazine treated MSN cells treated with okadaic acid.

Certain phenothiazines, for example, chlorpromazine, can markedly inhibit the expression of PHF epitopes (as determined by loss of immunoreactivity with Alzheimer's Disease specific antibodies) upon treatment of MSN1a cells with okadaic acid (cf. FIG. 3). These compounds are effective at micromolar concentrations, with increased potency being evident when cells are treated prior to the addition of okadaic acid. The effective concentrations appear to be in the range at which these drugs are present in the brain following chronic treatment of psychiatric patients (Svendsen, C N, Psychopharmacology, 90, 316–321, 1986). These results indicate that patients who were chronically treated with phenothiazines would be protected from the development of PHF, and thus would have a low probability of development of Alzheimer's Disease.

Figure 4A:
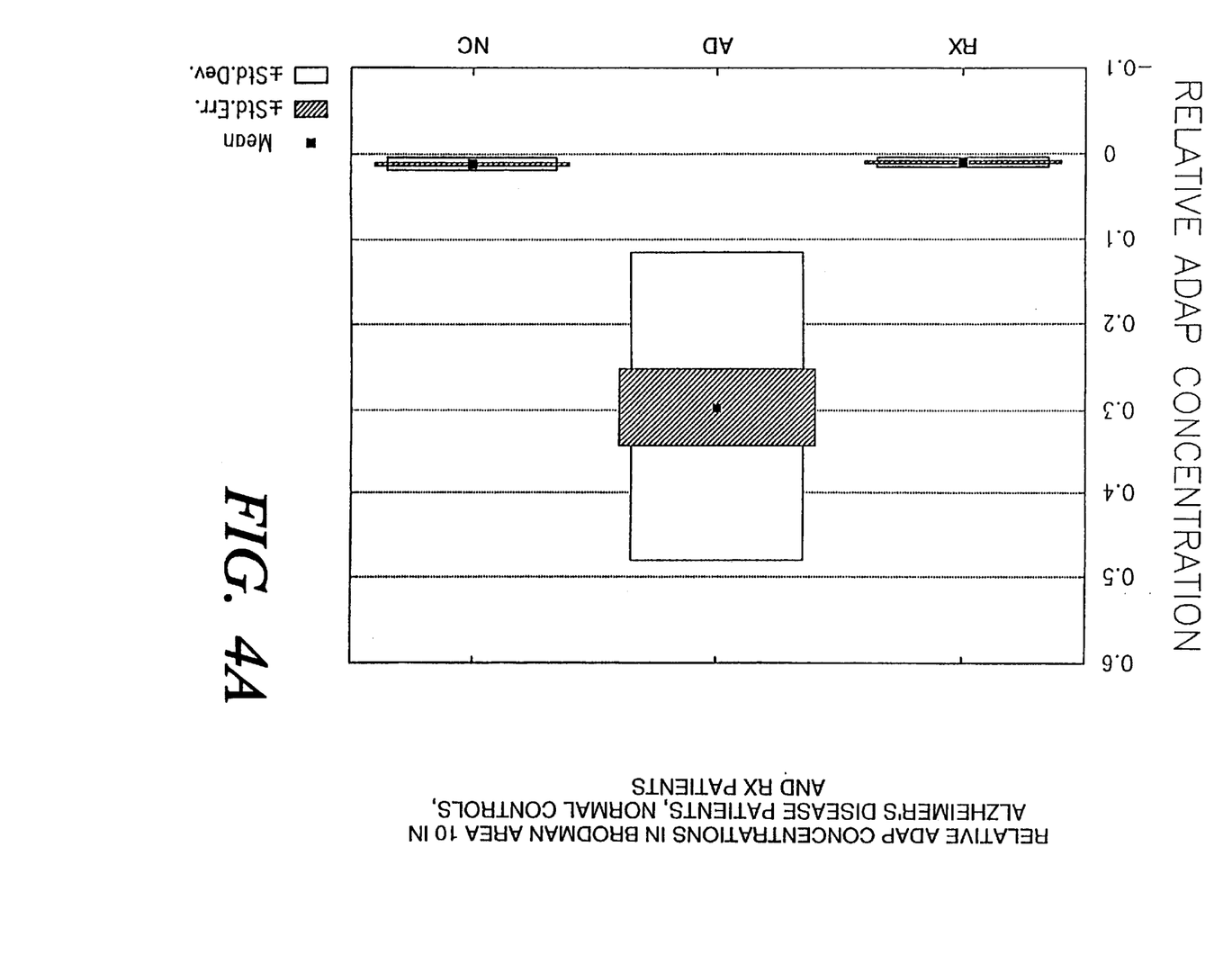
FIG. 4A is a chart showing relative ADAP concentrations in Brodman Area 10 in Alzheimer's Disease patients, normal controls and patients treated with chloropromazine (Rx).
Figure 4B:
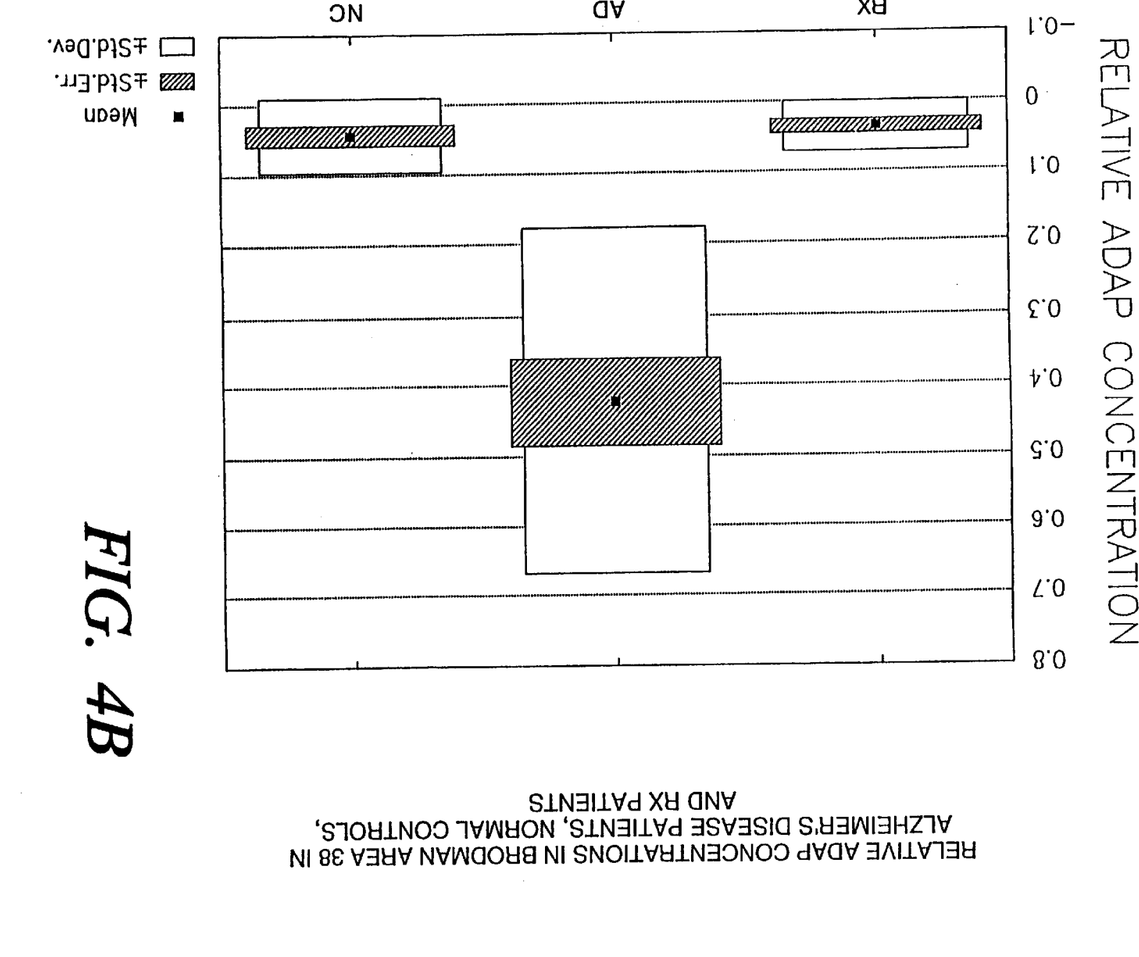
FIG. 4B is a chart showing relative ADAP concentrations in Brodman Area 38 in Alzheimer's Disease patients, normal controls and patients treated with chloropromazine (Rx).

Frontal and cortical brain tissue specimens obtained at autopsy from patients chronically treated with chlorpromazine were analyzed using the ALZ-EIA method previously described (Ghanbari, H A, et al, JAMA, 263, 2907, 1990). The results are shown in FIGS. 4A and 4B frontal (Broadman area 10) and temporal (Broadman area 38) regions, respectively. The brain tissue (post-mortem) from approximately the same number of (age matched) normal controls and Alzheimer's Disease patients were also analyzed and are presented in these figures as negative and positive controls (for normal and AD, respectively). As the data indicate, the samples from chlorpromazine treated patients (Rx) had low PHF epitope levels similar to normal controls, whereas the PHF epitope levels in the AD group were clearly much higher. Furthermore, these results were consistent with histopathological diagnosis of the brain specimens. Statistically, in the general population, about 20–30% of the individuals in the Rx age group would have developed AD and hence much higher PHF in the brain regions indicated (Katzman, R., Kawas, C. H., pages 105–122, in Alzheimer's Disease, Eds., Terry, R D; Katzman, R; Bick, K L. Raven Press, New York, 1994). This evidence shows that chronic treatment of patients with chlorpromazine prevents PHF formation and AD.

In a subsequent study, 51 additional patients were identified and the analysis was repeated as above using the TG3 antibody in an ELISA format. The results, summarized in Table 1, clearly reproduce and confirm the first retrospective study. Immunohistopathological studies carried out on several brain regions from these patients were consistent with these ELISA results. Taken together, these two studies provide evidence of the therapeutic benefit of chlorpromazine in AD and validate the use of the MSN1a model for the identification of therapeutically useful compounds for the treatment of AD.

TABLE 1

|  | N | MEAN AGE ± SEM | SIGNAL* ± SEM | |
|---|---|---|---|---|
|  |  |  | Frontal | Temporal |
| Normal | (12) | 79.50 ± 3.33 | 0.12 ± 0.12 | 0.00 ± 0.00 |
| AD | (28) | 82.54 ± 1.94 | 16.54 ± 2.59 | 17.55 ± 2.82 |
| Rx | (51) | 76.88 ± 1.55 | 0.12 ± 0.11 | 0.16 ± 0.11 |

* Signal is calculated by summing the means of duplicate absorbance readings (direct ELISA using TG3 antibody) for 8 dilutions of all lysates prepared by one to two serial dilutions.

Efforts to dissect the characteristic lesions of Alzheimer's Disease, namely the neurofibrillary tangles and the neuritic plaques have indicted that aberrant protein phosphorylation is a hallmark of the cytoskeletal abnormalities in AD. Phosphorylated sites on the PHFs found in neurofibrillary tangles and abnormal neurites are detected by AD-specific antibodies, such as TG3 and PHF-1, in the brains of AD patients and not in normal or other neurodegenerative disease controls (cf. FIG. 1, 2A). In the MSN1a cell culture model (cf. FIG. 2B, 3), these aberranty phosphorylated PHF sites are also detected by these antibodies.

Therefore, the therapeutic activity of the compounds of the invention was assessed by the ability of these agents to affect the production of abnormally phosphorylated epitopes pertinent to the production of PHFs of AD, utilizing a human neuroblastoma cell line (MSN1a) in the presence of the protein phosphatase inhibitor, okadaic acid (OKA). As described above, chlorpromazine, a clinically used antipyschotic, prevents production of the aberrantly phosphorylated PHF epitopes and, hence, the production of PHFs, thereby preventing AD. As shown in FIGS. 2B and 3, and in Table 2, chlorpromazine is effective in inhibiting the production of these aberrant phosphorylated epitopes in the MSN1a cell culture model as determined by the prevention of the immunoreactivity associated with PHF antibodies such as TG3 which was utilized in the retrospective clinical analysis.

To determine the effect of chlorpromazine on the paired helical filament epitopes associated with AD, MSN1a cells expressing paired helical filament epitopes were incubated with 100 mM chlorpromazine (CPZ) or a 0.2% DMSO vehicle control for 2 hours at 37° C. The cells were isolated by centrifugation, boiled for 10 minutes and 25 mg protein from the resulting heat stable supernatants were loaded per lane on an SDS-PAGE gel. The gel was electrophoretically transferred to nitrocellulose membrane and then immunostained with PHF-1. As shown in FIG. 3, CPZ greatly decreased the production of paired helical filament epitopes by the MSN1a cells. In contrast, the control shows that without the addition of CPZ, there was production of paired helical filament epitopes by the MSN1a cells. The use of the MSN1a cell culture model for screening of novel compounds for therapeutic activity in AD is, therefore, quite warranted.

This assay can thus be used to determine whether a drug is capable of preventing or intervening in AD by attenuating the production of abnormally phosphorylated paired helical filament epitopes associated with AD. To determine whether a drug is capable of preventing or intervening in AD activity, the MSN1a cells containing tau and associated proteins are treated with OKA capable of greatly increasing immunoreactivity of the MSN1a cells with AD specific monoclonal antibodies. Then, either prior to or concomitantly with OKA treatment, a compound of the present invention is added to the culture. If the compound prevents the induction of the AD epitopes in the MSN1a cells treated with OKA, then it is said to have anti-AD activity. If the AD-specific antibodies are highly reactive with the neuroblastoma cells following OKA treatment in the presence of compound, then the compound is said to be ineffectual against AD.

The MSN1a human neuroblastoma line was subcloned from a population of MSN cells obtained from the laboratory of Dr. Peter Davies (Albert Einstein College of Medicine, New York, N.Y.). Cells were grown and maintained in flasks in RPMI 1640 medium, supplemented with 15% fetal calf serum, 100 U/ml penicillin, 100 U/ml Streptomycin, 0.5 ug/ml fungizone under 7.5% $CO_2$ at 37° C.

Stock solutions of drugs were prepared by dissolving the anhydrous powders to final concentrations of either 10 or 20 mM in 50% aqueous or 100% dimethyl sulfoxide (DMSO), respectively. Working solutions of drugs were prepared by dilution of the stock solutions with Kreb's Ringer in Hepes buffer (KRH) (128 mM NaCl, 5 mM KCl, 2.5 mM $CaCl_2$ 1.2 mM $MgSO_4$, 1 mM $Na_2HPO_4$, 10 mM dextrose, 20 mM Hepes, pH 7.4). OKA is maintained as a 1 mM stock solution in DMSO prior to dilution to 4 $\mu$M in KRH.

MSN cells grown in 225 $cm^2$ flasks are removed from the incubator, their medium decanted and replaced with 50 ml pre-warmed KRH. The cells are harvested by scraping prior to sedimentation at 1000 rpm for 5 min. The supernatants are discarded and the cell pellets are resuspended, the cells counted and diluted to a density of $2 \times 10^4$ cells/50 ml. The cells are then plated in a 96 well plate at 50 $\mu$l/well and 25 $\mu$l of 4 AM OKA and 25 W of drug are then added to the appropriate wells; the entire 96 well plate is then incubated for 2 hrs at 37° C. Depending on the dilution of drug added, this yields individual wells containing 1 $\mu$M OKA, 0–64 $\mu$m drug and $2 \times 10^4$ cells in 0.26% DMSO in KRH. The incubation is terminated by the addition of 20 $\mu$l of 6× extraction buffer and immediate freezing at –80° C. for at least one hr. The 6× extraction buffer contains: 25 mM Tris-HCl, pH 7.6, 150 mM NaCl, 5 mM EDTA, 24 mM 5-glycerol phosphate, 10 $\mu$g/ml APMSF (4-amidinophenylmethane-sulfonyl flouride), and 2.5 $\mu$g/ml each of leupeptin, aprotinin, and pepstatin. The plates are thawed in a 37° C. water bath and 20 $\mu$l of cell lysate is added to a replica well in an ELISA plate that already contains 80 $\mu$l of coating buffer (15 mM $Na_2CO_3$ and 35 mM $NaHCO_3$, pH 9.6). The plates are allowed to coat overnight at 4° C. The plates are washed four times with deionized water and then blocked for 30 min at 37° C. with 200 μl/well pre-warmed 1% bovine serum albumin in 10 mM Tris-HCl, pH 7.4, 150 mM NaCl, 3 mM NaN₃ (BSA-TBS). After the blocking solution is removed, 100 μl/well of an appropriate dilution of pre-warmed primary antibody (eg., TG3 or PHF-1) in BSA-TBS is added and incubated at 37° C. for 30 min. Incubation is terminated by washing four times in deionized water at which time 100 μl of an appropriate dilution of pre-warmed secondary antibody (conjugated to alkaline phosphatase) in BSA-TBS is added to each well in the ELISA plate. Incubation is performed for 30 min at 37° C. followed by washing 4 times with deionized water. 100 μl/ml of prewarmed chromogenic substrate (1mg/ml p-nitrophenyl phosphate in 10% diethanolamnine, 3 mM NaN₃, 0.5 mM MgCl₂, pH 9.8) is added and the plate incubated for 30 min at 37° C. Absorbance at 405 nm is then determined by reading the plate on a BioRad UV Microplate Reader.

Results obtained from the MSN1a cell culture model studies utilizing the TG3 antibody are shown in Table 2 for a representative sample of compounds disclosed herein.

TABLE 2

| IC50 for inhibition of TG3 immunoreactivity in OKA treated MSN1a cells | |
|---|---|
| Example # | IC50 (μM) |
| Chlorpromazine | ~70.0 |
| 1 | 12.4 |
| 5 | 15.8 |
| 9 | 5.4 |
| 13 | 9.1 |
| 17 | 15.8 |
| 23 | 13.2 |
| 26 | 7.3 |
| 30 | 5.9 |
| 34 | 7.5 |
| 38 | 5.8 |
| 42 | 6.4 |
| 45 | 11.4 |

As seen in Table 2, the compounds of the present invention are potent inhibitors of the production of the aberrantly phosphorylated epitopes as detected in the MSN1a cell culture model system utilizing the antibody TG3. As shown, the compounds of the present invention are more potent than chlorpromazine, which was shown in the retrospective clinical study to both inhibit the production of the AD associated epitopes and prevent AD. The compounds of the present invention are thus useful in the treatment of AD.

What is claimed is:

1. A method of preventing Alzheimer's Disease in a patient in need of such treatment comprising administering to the patient an amount effective to inhibit formation of abnormally phosphorylated paired helical filament epitopes of a compound of the formula:

or a pharmaceutically acceptable salt thereof wherein:

$R_1$ is hydrogen, loweralkyl of 1 to 4 carbons, benzyl, phenyl or 2-, 3-, or 4-pyridyl;

$R_2$ and $R_3$ independently represent $C_1$–$C_8$ alkyl, $C_2$–$C_8$ alkenyl or $C_3$–$C_8$ cycloalkyl, phenyl, halogenated-phenyl or loweralkoxyphenyl;

$R_4$ is hydrogen or $C_1$–$C_4$ alkyl attached to carbon atom 6 or 7 of the indole nucleus; and X and Y independently represent lower alkyl, hydroxy lower alkyl, lower acyloxy alkyl, carbamoyloxy lower alkyl, and phenyl lower alkyl.

2. A method of preventing Alzheimer's Disease in a patient in need of such treatment comprising administering to the patient an amount effective to inhibit formation of abnormally phosphorylated paired helical filament epitopes of a compound of the formula:

or a pharmaceutically acceptable salt thereof wherein:

$R_1$ is hydrogen, loweralkyl of 1 to 4 carbons, benzyl, phenyl or 2-, 3-, or 4-pyridyl;

$R_2$ and $R_3$ independently represent $C_1$–$C_8$ alkyl, $C_2$–$C_8$ alkenyl or $C_3$–$C_8$ cycloalkyl, phenyl, halogenated-phenyl or loweralkoxyphenyl;

$R_4$ is hydrogen or $C_1$–$C_4$ alkyl attached to carbon atom 6 or 7 of the indole nucleus; and represents a heterocyclic ring having up to 8 members.

* * * * *